United States Patent
An et al.

(10) Patent No.: US 11,576,620 B2
(45) Date of Patent: Feb. 14, 2023

(54) MULTI-DISEASE PATIENT MANAGEMENT

(71) Applicant: Cardiac Pacemakers, Inc., St. Paul, MN (US)

(72) Inventors: Qi An, Blaine, MN (US); Pramodsingh Hirasingh Thakur, Woodbury, MN (US); Viktoria A. Averina, Shoreview, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 588 days.

(21) Appl. No.: 15/471,583

(22) Filed: Mar. 28, 2017

(65) Prior Publication Data
US 2017/0281095 A1 Oct. 5, 2017

Related U.S. Application Data

(60) Provisional application No. 62/317,003, filed on Apr. 1, 2016.

(51) Int. Cl.
*A61B 5/00* (2006.01)
*A61B 5/0205* (2006.01)
(Continued)

(52) U.S. Cl.
CPC .............. *A61B 5/7275* (2013.01); *A61B 5/02* (2013.01); *A61B 5/0205* (2013.01);
(Continued)

(58) Field of Classification Search
CPC ........ A61B 5/0205; A61B 5/08; A61B 5/7275
See application file for complete search history.

(56) References Cited

U.S. PATENT DOCUMENTS 6,409,675 B1   6/2002   Turcott
6,440,066 B1*  8/2002   Bardy ................. A61B 5/0002
                                                  600/300
(Continued)

FOREIGN PATENT DOCUMENTS

CN   102216951 A   10/2011
CN   105228513 A   1/2016
(Continued)

OTHER PUBLICATIONS

Federico P. Gomez, MD, and Roberto Rodriguez-Roisin, MD, Global Initiative for Chronic Obstructive Lung Disease (GOLD) guidelines for chronic obstructive pulmonary disease, 2002, ISSN 1070-5287 Lippincott Williams & Wilkins, Inc. (Year: 2002).*
(Continued)

*Primary Examiner* — Eric J Messersmith
(74) *Attorney, Agent, or Firm* — Schwegman Lundberg & Woessner, P.A.

(57) ABSTRACT

Systems and methods for monitoring patients with multiple chronic diseases are described. A system may include a health status monitor that receives diagnostic data including physiological signals sensed from a patient. The system may produce at least a first risk indication of the patient developing a first disease and a second risk indication of the patient developing a different second disease. The system may detect the first and second diseases from the physiological signals, and generate a composite health status indicator using the detections of the first and second diseases and the first and second risk indications. An alert of worsening health status may be generated if the composite detection score exceeds an alert threshold.

20 Claims, 5 Drawing Sheets

(51) Int. Cl.
  *A61B 5/02* (2006.01)
  *G16H 50/30* (2018.01)
  *G16H 40/63* (2018.01)
  *A61B 5/08* (2006.01)
  *A61B 5/20* (2006.01)
  *G16H 20/10* (2018.01)

(52) U.S. Cl.
  CPC ............ *A61B 5/02028* (2013.01); *A61B 5/08* (2013.01); *A61B 5/201* (2013.01); *A61B 5/746* (2013.01); *G16H 40/63* (2018.01); *G16H 50/30* (2018.01); *A61B 5/0022* (2013.01); *A61B 2505/07* (2013.01); *G16H 20/10* (2018.01)

(56) References Cited

U.S. PATENT DOCUMENTS

| | | | | |
|---|---|---|---|---|
| 8,579,824 B2* | 11/2013 | Cho | A61B 5/0215 | 600/483 |
| 10,278,653 B2* | 5/2019 | Averina | A61B 5/686 | |
| 10,786,408 B2* | 9/2020 | Sidhu | A61B 5/1115 | |
| 2003/0233031 A1 | 12/2003 | Rice | | |
| 2006/0074334 A1* | 4/2006 | Coyle | A61B 5/398 | 600/529 |
| 2007/0073555 A1* | 3/2007 | Buist | G16H 40/20 | 600/300 |
| 2008/0126124 A1* | 5/2008 | Schechter | G16H 50/30 | 705/2 |
| 2008/0228090 A1* | 9/2008 | Wariar | A61B 5/145 | 600/508 |
| 2009/0264779 A1* | 10/2009 | Snider | G01N 33/6869 | 600/508 |
| 2010/0030292 A1* | 2/2010 | Sarkar | A61N 1/36521 | 607/6 |
| 2012/0041279 A1* | 2/2012 | Freeman | G16H 20/40 | 600/301 |
| 2012/0109243 A1* | 5/2012 | Hettrick | A61B 5/686 | 607/17 |
| 2012/0157797 A1* | 6/2012 | Zhang | A61B 5/318 | 600/301 |
| 2012/0173264 A1 | 7/2012 | Brush et al. | | |
| 2012/0253207 A1* | 10/2012 | Sarkar | A61B 5/7275 | 600/483 |
| 2012/0277546 A1* | 11/2012 | Soykan | A61B 5/318 | 600/301 |
| 2013/0030258 A1* | 1/2013 | Cheung | G16H 50/20 | 600/301 |
| 2013/0066643 A1* | 3/2013 | Seward | G16H 70/60 | 705/2 |
| 2013/0116578 A1* | 5/2013 | An | A61B 5/4842 | 600/484 |
| 2013/0197381 A1* | 8/2013 | Charlton | A61B 5/341 | 600/523 |
| 2013/0267791 A1* | 10/2013 | Halperin | A61B 5/6892 | 600/300 |
| 2014/0088442 A1* | 3/2014 | Soykan | A61B 5/0031 | 600/483 |
| 2014/0276164 A1* | 9/2014 | Thakur | A61B 5/686 | 600/528 |
| 2014/0343438 A1* | 11/2014 | Sweeney | A61B 5/4818 | 600/483 |
| 2014/0343439 A1* | 11/2014 | Sweeney | A61B 5/024 | 600/484 |
| 2015/0040685 A1* | 2/2015 | Nicholson | G01L 1/2206 | 73/862.51 |
| 2015/0157273 A1 | 6/2015 | An et al. | | |
| 2015/0186607 A1* | 7/2015 | Geleijnse | G16H 50/20 | 705/2 |
| 2015/0250428 A1* | 9/2015 | Zhang | A61B 5/4842 | 600/301 |
| 2016/0106345 A1* | 4/2016 | Kostic | A61B 5/1115 | 5/428 |
| 2016/0259910 A1* | 9/2016 | Averina | G06T 11/206 | |
| 2016/0361026 A1* | 12/2016 | Sarkar | A61B 5/742 | |
| 2017/0100081 A1* | 4/2017 | Thakur | A61N 1/3962 | |
| 2017/0213437 A1* | 7/2017 | Sundaram | G16H 40/67 | |

FOREIGN PATENT DOCUMENTS

| | | | | |
|---|---|---|---|---|
| CN | 105246397 B | 5/2018 | | |
| CN | 109152529 A | 1/2019 | | |
| CN | 109152529 B | 10/2021 | | |
| EP | 1102200 A2 * | 5/2001 | ........... A61B 5/0002 |
| WO | WO-2010144336 A2 | 12/2010 | | |
| WO | WO-2012057860 A1 | 5/2012 | | |
| WO | WO-2013006629 A1 | 1/2013 | | |
| WO | WO-2017172755 A1 | 10/2017 | | |

OTHER PUBLICATIONS

Andrew S. Levey, Kai-Uwe Eckardt, Yusuke Tsukamoto, Definition and classification of chronic kidney disease: A position statement from Kidney Disease: Improving Global Outcomes (KDIGO), Feb. 28, 2005, Kidney International, vol. 67 (2005), pp. 2089-2100 (Year: 2005).*

"European Application Serial No. 17716714.5, Response Filed May 23, 2019 to Communication pursuant to Rules 161(2) and 162 EPC dated Nov. 16, 18", 12 pgs.

"International Application Serial No. PCT/US2017/024521, International Preliminary Report on Patentability dated Oct. 11, 2018", 8 pgs.

"International Application Serial No. PCT/US2017/024521, International Search Report dated Jun. 29, 2017", 5 pgs.

"International Application Serial No. PCT/US2017/024521, Written Opinion dated Jun. 29, 2017", 8 pgs.

"Chinese Application Serial No. 201780022374.5, Office Action dated Oct. 21, 2020", w/English translation, 22 pgs.

"European Application Serial No. 17716714.5, Communication pursuant to Article 94(3) EPC dated Sep. 28, 2020", 6 pgs.

"Chinese Application Serial No. 201780022374.5, Office Action dated Mar. 24, 2021", w/English translation, 20 pgs.

"European Application Serial No. 17716714.5, Response filed Jan. 19, 2021 to Communication pursuant to Article 94(3) EPC dated Sep. 28, 2020", 14 pgs.

"Chinese Application Serial No. 201780022374.5, Response filed Jun. 7, 2021 to Office Action dated Mar. 24, 2021", w/ English Claims, 20 pgs.

* cited by examiner

MULTI-DISEASE PATIENT MANAGEMENT

CLAIM OF PRIORITY

This application claims the benefit of priority under 35 U.S.C. §119(e) of U.S. Provisional Patent Application Ser. No. 62/317,003, filed on Apr. 1, 2016, which is herein incorporated by reference in its entirety.

TECHNICAL FIELD

This document relates generally to medical devices, and more particularly, to systems and methods for monitoring patients having medical device.

BACKGROUND

Congestive heart failure (CHF) is a leading cause of death in the United States. CHF occurs when the heart is unable to adequately supply enough blood to maintain a healthy physiological state. CHF may be treated by drug therapy, or by an implantable medical device (MD) such as for providing cardiac electrostimulation therapies, including resynchronization therapy (CRT) to correct cardiac dyssynchrony within a ventricle or between ventricles.

CHF patients may exhibit various comorbidities, including Chronic Obstructive Pulmonary Disease (COPD), asthma, diabetes, or renal disease. In some patients, multiple disease conditions may interact with each other, such that worsening of one disease may adversely impacts progression of other disease states, causing systemic deterioration of patient health status. For example, some of the HF comorbidities may worsen along with the progression of CHF, such as exacerbation of the COPD or other pulmonary disease, or acute kidney failure. Additionally, some CHF patients may have be exposed to higher risk than other CHF patients of developing certain comorbidities.

CHF may have a huge economic impact on the healthcare system. Patients hospitalized with worsened heart failure such as decompensated heart failure may have a high rate of rehospitalization for various causes such as development or worsening of HF comorbidities. Proper patient monitoring, such as identification of patient at higher risks of developing a future event of WHF or HF comorbidities, and accurate detection of precursor events related to WHF event or HF comorbidities may allow proper and timely treatment and patient management, which may reduce the rehospitalization rate and the associated cost.

SUMMARY

This document discusses, among other things, a patient management system for monitoring patients with multiple chronic diseases. The system may include a health status monitor that receives diagnostic data including physiological signals sensed from a patient. The system may produce at least a first risk indication of the patient developing a first disease and a second risk indication of the patient developing a different second disease. The first and the second disease may include a cardiac, pulmonary, or renal disease. The system may detect the first and second diseases from the physiological signals, and generate a composite health status indicator using the detections of the first and second diseases and the first and second risk indications. An alert of worsening health status may be generated if the composite detection score exceeds an alert threshold.

In Example 1, a system for monitoring health status of a patient is disclosed. The system may comprise a physiological sensor circuit including a sense amplifier circuit to sense one or more physiological signals, a health status analyzer circuit coupled to the physiological sensor circuit, and an output circuit. The health status analyzer circuit may include a risk stratifier circuit to produce a first risk indication of the patient developing a first disease and a second risk indication of the patient developing a different second disease, a first detector circuit to detect the first disease from the one or more physiological signals, a second detector circuit to detect the second disease from the one or more physiological signals, and a blending circuit to generate a composite health status indicator using the detections of the first and second diseases and the first and second risk indications. The output circuit configured to generate a human-perceptible presentation of the composite health status indicator.

Example 2 may include, or may optionally be combined with the subject matter of Example 1 to optionally include, the first detector circuit to detect the first disease including a future worsening heart failure (WHF) event and the second detector circuit to detect the second disease including a heart failure co-morbidity which may include a future pulmonary disease or future renal disease.

Example 3 may include, or may optionally be combined with the subject matter of Example 2 to optionally include, a third detector circuit to detect a third disease different from the first and second diseases. The risk stratifier circuit may produce a third risk indication of the patient developing a third disease. At least one of the first, second, or third detector circuit may detect the respective first, second, or third disease from the one or more physiological signals using one or more of the first, second, and third risk indications, and the blending circuit may produce the composite health status indicator further using the detection of the third disease and the third risk indication.

Example 4 may include, or may optionally be combined with the subject matter of one or any combination of Examples 2 or 3 to include, the risk stratifier circuit that may generate the second risk indication of the patient developing a future pulmonary disease using both primary and secondary pulmonary risk indications. The primary pulmonary risk indication may be based on a first pulmonary signal metric and the secondary pulmonary risk indication may be based on second and third pulmonary signal metrics.

Example 5 may include, or may optionally be combined with the subject matter of Example 4 to optionally include, the risk stratifier circuit that may be configured to generate the secondary pulmonary risk indication using the second pulmonary signal metric weighted by the third pulmonary signal metric.

Example 6 may include, or may optionally be combined with the subject matter of one or any combination of Examples 4 or 5 to include, the risk stratifier circuit that may be configured to generate the secondary pulmonary risk indication using a plurality of measurements of the second pulmonary signal metric when the third pulmonary signal metric satisfies a specified condition.

Example 7 may include, or may optionally be combined with the subject matter of one or any combination of Examples 1 through 6 to include, at least one of the first detector circuit that may be configured to detect the first disease in response to the first risk indication exceeding a first risk threshold, or the second detector circuit that may be configured to detect the second disease in response to the second risk indication exceeding a second risk threshold.

Example 8 may include, or may optionally be combined with the subject matter of one or any combination of Examples 1 through 7 to include, the first detector configured to detect the first disease and the second detector configured to withhold detection of the second disease in response to the first risk indication being substantially higher than the second risk indication, or the second detector configured to detect the second disease and the first detector configured to withhold detection of the first disease in response to the second risk indication being substantially higher than the first risk indication.

Example 9 may include, or may optionally be combined with the subject matter of one or any combination of Examples 1 through 8 to include, at least one of the first or second detector circuit that may be configured to detect the first or second disease according to a first operating mode if the first or second risk indication exceeds a risk threshold, and to detect the first or second disease according to a second operating mode if the first or second risk indication does not exceed the risk threshold. The first operating mode includes a first detection algorithm and the second operating mode includes a second detection algorithm, and the first detection algorithm may be more sensitive or less specific to the first or second disease than the second algorithm.

Example 10 may include, or may optionally be combined with the subject matter of Example 9 to optionally include, the operating mode for detecting the respective first or second disease that is based on a joint risk pattern including the first risk indication relative to the second risk indication.

Example 11 may include, or may optionally be combined with the subject matter of one or any combination of Examples 1 through 10 to include, the first risk indication including a first risk score and a second risk indication including a second risk score. The first detector circuit may detect the first disease including generate a first detection score indicating a confidence of detecting the first disease. The second detector circuit may detect the second disease including generate a second detection score indicating a confidence of detecting the second disease. The blending circuit may produce the composite health status indicator including a composite detection score using a combination of the first and second detection scores each weighted by the respective first and second risk scores.

Example 12 may include, or may optionally be combined with the subject matter of Example 11 to optionally include, the output circuit that may generate an alert of worsening health status if the composite detection score exceeds an alert threshold.

Example 13 may include, or may optionally be combined with the subject matter of Example 12 to optionally include, the health status analyzer circuit that may be configured to increase the alert threshold if the first or second risk indication indicates respectively a low risk of developing the first or second disease, and decrease the alert threshold if the first or second risk indication indicates respectively a high risk of developing the first or second disease.

Example 14 may include, or may optionally be combined with the subject matter of one or any combination of Examples 11 through 13 to include, the risk stratifier circuit that may be configured to produce the first or second risk score using information about a classification of the first or second disease. The classification may include a classification of a worsening heart failure (WHF) event into one of New York Heart Failure classes one through four, a classification of a pulmonary disease into one of Chronic Obstructive Pulmonary Disease stages one through four, or a classification of a chronic kidney disease (CKD) into one of CKD stages one through five.

Example 15 may include, or may optionally be combined with the subject matter of one or any combination of Examples 1 through 14 to include, the risk stratifier circuit that may be configured to determine the first or second risk indication based on a medical history of the patient.

In Example 16, a system for identifying a patient's risk of developing a future worsening pulmonary disease is disclosed. The system may comprise sensor circuits, a signal processor circuit, a risk stratifier circuit coupled to the signal processor circuit, and an output circuit. The sensor circuits may include a first sense amplifier circuit to sense a first physiological signal, a second sense amplifier circuit to sense a second physiological signal, and a third sense amplifier circuit to sense a third physiological signal. The signal processor circuit may include filter circuits to generate a first signal metric from the first physiological signal, a second signal metric from the second physiological signal, and a third signal metric from the second physiological signal. The risk stratifier circuit may generate a primary pulmonary risk indication using at least the first signal metric and a secondary pulmonary risk indication using at least the second signal metric modulated by the third signal metrics. The modulation may include multiplying the second signal metric by the third signal metric, or sampling the second signal metric conditional upon the third signal metric satisfying a specified condition. The output circuit may provide the composite cardiac risk indication to a clinician or a process.

In Example 17, a method for monitoring health status of a patient using a monitor system is disclosed. The method may include steps of sensing one or more physiological signals; generating a first risk indication of the patient developing a first disease and a second risk indication of the patient developing a different second disease; detecting the first and second diseases from the one or more physiological signals; computing a composite health status indicator using the detections of the first and second diseases and the first and second risk indications; and generating a human-perceptible presentation of the composite health status indicator.

Example 18 may include, or may optionally be combined with the subject matter of Example 17 to optionally include, the method of detecting the first disease is a future worsening heart failure (WHF) event, and detecting the second disease is a heart failure co-morbidity including a future pulmonary disease or future renal disease.

Example 19 may include, or may optionally be combined with the subject matter of Example 18 to optionally include, steps of detecting a third disease different from the first and second diseases, and generating a third risk indication of the patient developing the third disease. The composite health status indicator may be computed further using the detection of the third disease and the third risk indication.

Example 20 may include, or may optionally be combined with the subject matter of Example 17 to optionally include, the method of detecting the first and second diseases that may include detecting the first disease and withholding detection of the second disease in response to the first risk indication being substantially higher than the second risk indication, or detecting the second disease and withholding detection of the first disease in response to the second risk indication being substantially higher than the first risk indication.

Example 21 may include, or may optionally be combined with the subject matter of Example 17 to optionally include, the method of detecting the first or second diseases that may include detecting the first or second disease according to a first operating mode if the first or second risk indication exceeds a risk threshold, and detecting the first or second disease according to a second operating mode if the first or second risk indication does not exceed the risk threshold. The first operating mode includes a first detection algorithm and the second operating mode includes a second detection algorithm, where the first detection algorithm mat be more sensitive or less specific to the first or second disease than the second algorithm.

Example 22 may include, or may optionally be combined with the subject matter of Example 17 to optionally include, the method of detecting the first and second diseases including generating a first detection score indicating a confidence of detecting the first disease and a second detection score indicating a confidence of detecting the second disease. The composite health status indicator may be computed using a combination of the first and second detection scores each weighted by the respective first and second risk indications.

Example 23 may include, or may optionally be combined with the subject matter of Example 17 to optionally include, steps of determining an alert threshold using at least one of the first or second risk indication, and generating an alert of worsening health status if the composite detection score exceeds the alert threshold.

The systems, devices, and methods discussed in this document may improve the medical technology of automated monitoring of patient with multiple chronic diseases, and prevention of worsening of heart failure or heart failure co-morbidities such as pulmonary or renal diseases. A composite health status indicator that is based on detection of various chronic diseases and identification of various risk factors may enhance the performance and functionality of a patient monitoring system or an ambulatory medical device. In certain examples, the enhanced device functionality may include more timely detection of worsening health conditions with increased accuracy (e.g., lower false positive detections) at little to no additional cost. The improvement in system performance and functionality, provided by the present systems and methods, can reduce healthcare costs associated with management and hospitalization of patients with chronic diseases. The systems, devices, and methods discussed in this document also allow for more efficient device memory usage, such as by storing risk indications associated with various chronic diseases that are clinically relevant to patient health status assessment. As fewer false positive detections are provided, device battery life can be extended, fewer unnecessary drugs and procedures may be scheduled, prescribed, or provided, and an overall system cost savings may be realized.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring patients with multiple disease conditions and assessing the patient health status. A system described herein may assess a patient's risk of developing multiple diseases in the future, and detect multiple diseases using physiological signals sensed from the patient. The disease detection may be based on the risk assessment of multiple diseases. A composite health status indicator may be generated using a combination of the detections of diseases and the risk assessment. An alert of worsening health status may be generated if the composite detection score exceeds an alert threshold.

Figure 1:
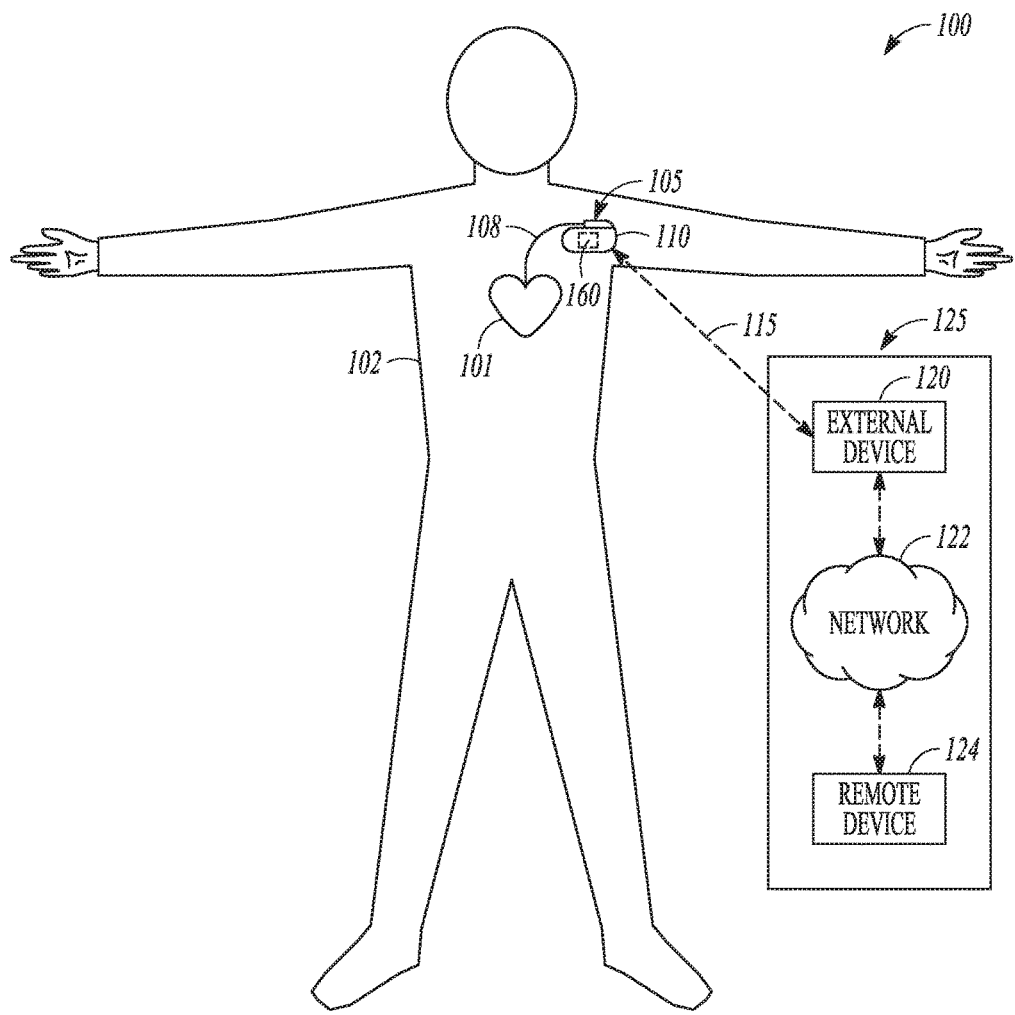
FIG. 1 illustrates generally an example of a patient management system and portions of an environment in which the patient management system may operate.

FIG. 1 illustrates generally an example of a patient management system 100 and portions of an environment in which the patient management system 100 may operate. The patient management system 100 may include an ambulatory system 105 associated with a patient body 102, an external system 125, and a telemetry link 115 providing for communication between the ambulatory system 105 and the external system 125.

The ambulatory system 105 may include an ambulatory medical device (AMD) 110 and a therapy delivery system such as a lead system 108. The AMD 110 may include an implantable device that may be implanted within the body 102 and coupled to a heart 101 via the lead system 108. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices, or patient monitors, among others. The AMD 110 may alternatively or additionally include subcutaneously implanted devices such as a subcutaneous ICD or a subcutaneous diagnostic device, wearable medical devices such as patch based sensing device, or other external monitoring or therapeutic medical devices such as a bedside monitor.

The lead system 108 may include one or more transvenously, subcutaneously, or non-invasively placed leads or catheters. Each lead or catheter may include one or more electrodes for delivering pacing, cardioversion, defibrillation, neuromodulation, drug therapies, or biological therapies, among other types of therapies. In an example, the electrodes on the lead system 108 may be positioned inside or on a surface of at least a portion of the heart, such as a right atrium (RA), a right ventricle (RV), a left atrium (LA), a left ventricle (LV), or any tissue between or near the heart portions. The arrangements and uses of the lead system 108 and the associated electrodes may be determined based on the patient need and the capability of the AMD 110. In some examples, the AMD 110 may include one or more un-tethered electrodes associated with an outer surface of the AMD 110, and the AMD 110 and the associated un-tethered electrodes may be configured to be deployed to a target cardiac site or other tissue site.

The AMD 110 may house an electronic circuit for sensing a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, intracardiac acceleration, physical activity or exertion level, physiological response to activity, posture, respiration, body weight, or body temperature. The AMD 110 may initiate or adjust therapies based on the sensed physiological signals.

The patient management system 100 may include a health status monitor 160 for patient management based on at least diagnostic data acquired by the ambulatory system 105. The health status monitor 160 may analyze the diagnostic data for patient monitoring, risk stratification, and detection of events such as worsening heart failure (WHF) or one or more HF comorbidities. In a non-limiting example as illustrated in FIG. 1, the health status monitor 160 may be substantially included in the AMD 110. Alternatively, the health status monitor 160 may be substantially included in the external system 125, or be distributed between the ambulatory system 105 and the external system 125.

The external system 125 may be used to program the AMD 110. The external system 125 may include a programmer, or a patient management system that may access the ambulatory system 105 from a remote location and monitor patient status and/or adjust therapies. By way of example and not limitation, and as illustrated in FIG. 1, the external system 125 may include an external device 120 in proximity of the AMD 110, a remote device 124 in a location relatively distant from the AMD 110, and a telecommunication network 122 linking the external device 120 and the remote device 124. The telemetry link 115 may be an inductive telemetry link, or a radio-frequency (RF) telemetry link. The telemetry link 115 may provide for data transmission from the AMD 110 to the external system 125. This may include, for example, transmitting real-time physiological data acquired by the AMD 110, extracting physiological data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more of acquiring physiological data, performing at least one self-diagnostic test (such as for a device operational status), delivering at least one therapy, or analyzing data associated with patient health conditions such as progression of heart failure.

Portions of the AMD 110 or the external system 125 may be implemented using hardware, software, or any combination of hardware and software. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
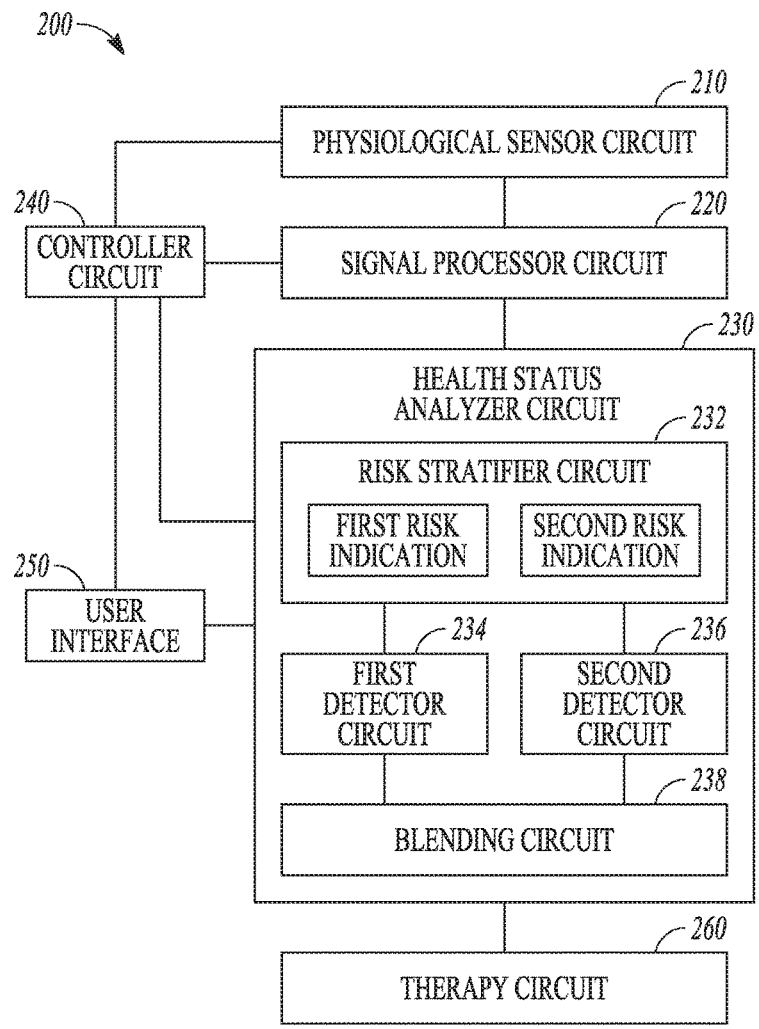
FIG. 2 illustrates generally an example of a patient monitoring system for assessing a patient's health status.

FIG. 2 illustrates generally an example of a patient monitoring system 200 for assessing a patient's health status. The patient monitoring system 200 may be used to detect progression of multiple diseases, including worsening heart failure, HF comorbidities, or other concomitant diseases in HF patients. As illustrated in FIG. 2, the patient monitoring system 200 may include one or more of a physiological sensor circuit 210, a signal processor circuit 220, a health status analyzer circuit 230, a controller circuit 240, and a user interface 250. At least a portion of the patient monitoring system 200 may be implemented within the AMD 110, distributed between two or more implantable or wearable medical devices (such as an implantable medical device and a subcutaneous medical device), or distributed between the AMD 110 and the external system 125.

The physiological sensor circuit 210 may include a sense amplifier circuit to sense one or more physiological signals indicative of intrinsic physiological activities, evoked physiological activities when the heart is stimulated in accordance with a specified stimulation configuration, or physiological activities under other specified conditions. The physiological sensor circuit 210 may be coupled to one or more electrodes such as on the lead system 108, or one or more implantable, wearable, or other ambulatory physiological sensors, to sense the physiological signal(s). Examples of physiological sensors may include pressure sensors, flow sensors, impedance sensors, accelerometers, microphone sensors, respiration sensors, temperature sensors, or blood chemical sensors, among others. Examples of the physiological signals sensed by the physiological sensor circuit 210 may include electrocardiograph (ECG), an electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, central venous pH value, a heart sound (HS) signal, a posture signal, a physical activity signal, a biomarker signal, or a respiration signal, among others. The physiological sensor circuit 210 may additionally or alternatively be coupled to a storage device that stores the physiological information, such as an external programmer, an electronic medical record (EMR) system, or a memory unit, among other data storage devices.

The signal processor circuit 220, coupled to the physiological sensor circuit 210, may include a filter circuit to filter the sensed physiological signal to produce a trend of a signal metric. The signal metric may include statistical parameters extracted from the sensed physiological signal, such as signal mean, median, or other central tendency measures or a histogram of the signal intensity, among others. In an example, the signal metric may include morphological parameters extracted from the sensed physiological signal, such as maximum or minimum within a specified time period such as a cardiac cycle, positive or negative slope or higher order statistics, signal power spectral density at a specified frequency range, among other morphological descriptors. In an example, a thoracic or cardiac impedance signal may be sensed using the electrodes on the lead system 108, and impedance metrics may include thoracic impedance magnitude within a specified frequency range obtained from. In an example, a heart sound signal may be sensed from an accelerometer, a microphone, or an acoustic sensor coupled to the AMD 110, and HS metrics may include intensities of heart sound components including first (S1), second (S2), third (S3), or fourth (S4) heart sounds or a relative intensity such as a ratio between two heart sound components, or timing of the S1, S2, S3, or S4 heart sound with respect to a fiducial point such as a P wave, Q wave, or R wave in an ECG. In an example, a respiration signal may be sensed using an impedance sensor or an accelerometer, and the respiratory metric may include a respiratory rate, a tidal volume, or a rapid-shallow breathing index (RSBI) computed as a ratio of a respiration rate to a tidal volume. In another example, a physical activity signal may be sensed using an accelerometer, and the activity metrics may include physical activity intensity, or a time duration when the activity intensity is within a specified range or above a specified threshold. In yet another example, the physiological sensor circuit 210 may receive a blood pressure signal from a pressure sensor, and the pressure metrics may include systolic blood pressure, diastolic blood pressure, mean arterial pressure, and the timing metrics of these pressure measurements with respect to a fiducial point.

Multiple measurements of the signal metric during a period of time may form a signal metric trend. In an example, the signal metric trend may include a daily trend including daily measurement of a signal metric over a specified number of days. Each daily measurement may be determined as a central tendency of a plurality of measurements obtained within a day. In an example, a thoracic impedance trend may be generated using portions of the received impedance signal during identical phases of a cardiac cycle such as within a certain time window relative to R-wave in a ECG signal), or at identical phases of a respiratory cycle such as within an inspiration phase or an expiration phase of a respiration signal. This may minimize or attenuate the interferences such as due to cardiac or respiratory activities, in the impedance measurements. The thoracic impedance trend may be generated using impedance measurements collected during one or more impedance acquisition and analysis sessions. In an example, an impedance acquisition and analysis session may start between approximately 5 a.m. and 9 a.m. in the morning, and lasts for approximately 2-8 hours. In another example, the impedance acquisition and analysis session may be programmed to exclude certain time periods, such as night time, or when the patient is asleep. The impedance parameter may be determined as a median of multiple impedance measurements acquired during the impedance acquisition and analysis session.

The health status analyzer circuit 230, coupled to the signal processor circuit 220, may be configured to detect from one or more physiological signals at least first and second diseases. The first and second diseases may each indicate an onset of a disease, worsening of a disease state, or a change of a disease state. In some examples, the health status analyzer circuit 230 may be configured to detect a third disease different than first and second disease. In an example, the first disease may be a cardiac disease such as WHF event, and the second or third disease may each include a HF comorbidity, such as a pulmonary disease (e.g., pulmonary edema, pneumonia, or COPD), a renal disease (e.g., acute kidney failure), a cardiac arrhythmia (e.g., atrial fibrillation or ventricular arrhythmias), diabetes mellitus, or hypertension, among others. The health status analyzer circuit 230 may generate a composite health status indicator using the detections of the first and second diseases. In some examples, the health status analyzer circuit 230 may determine a first risk indication of the patient developing a first disease and a second risk indication of the patient developing a different second disease, and generate the composite health status indicator using the first and second risk indications. In some examples, the composite health status indicator may be generated using the detections of the first and second diseases and the first and second risk indications.

The health status analyzer circuit 230 may be implemented as a part of a microprocessor circuit. The microprocessor circuit may be a dedicated processor such as a digital signal processor, application specific integrated circuit (ASIC), microprocessor, or other type of processor for processing information including the physiological signals received from the physiological sensor circuit 210. Alternatively, the microprocessor circuit may be a general purpose processor that may receive and execute a set of instructions of performing the functions, methods, or techniques described herein.

The health status analyzer circuit 230 may include circuit sets comprising one or more other circuits or sub-circuits, such as a risk stratifier circuit 232, a first detector circuit 234, a second detector circuit 236, and a blending circuit 238, as illustrated in FIG. 2. The health status analyzer circuit 230 may further include a third detector circuit (not shown). These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The risk stratifier circuit 232 may produce risk indications indicating the patient risks for developing multiple diseases or worsening of different disease states in the future. The risk indications may include at least a first risk indication ($R_1$) indicating the risk of the first disease, and a second risk indication ($R_2$) indicating the risk of the different second disease. In an example, the risk indications may further include a third risk indication ($R_3$) indicating the risk of the third disease different from the first and second diseases. One or more of the risk indications may be provided by a system user such as via the user interface 250, or at least partially automatically retrieved by the health status analyzer circuit 230 from a memory that stores the patient's up-to-date risk information. In an example, the risk stratifier circuit 232 may determine one or more risk indicators by analyzing the one or more physiological signals. For example, the risk stratifier circuit 232 may determine a risk of future cardiac event (such as a WHF event) using one or more signal metrics generated by the signal processor circuit 220. Examples of the signal metrics for assessing the cardiac event risk may include intensity of a heart sound component such as S3 heart sound intensity measured from a heart sound signal, a respiration rate or tidal volume measured from a respiration signal, thoracic impedance measured from an impedance signal such as using electrodes on one or more implantable leads and implantable device can housing, or physical activity intensity measured from an physical activity signal sensed with an ambulatory accelerometer associated with the patient.

Figure 4:
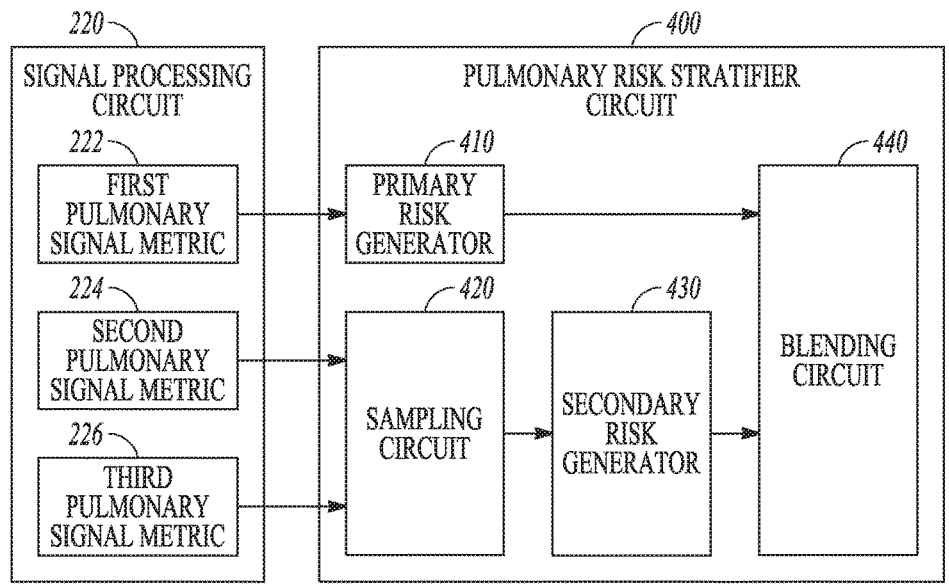
FIG. 4 illustrates generally an example of a pulmonary risk stratifier circuit for assessing the patient risk of developing a future pulmonary disease.

The risk stratifier circuit 232 may additionally use one or more signal metrics generated by the signal processor circuit 220 to determine a risk of future pulmonary disease such as COPD, asthma, pulmonary edema, or pulmonary hypertension, or to determine a risk of future renal disease such as chronic kidney failure. The signal metrics for assessing the risk of one disease (such as WHF) may also be used for assessing the risk of another different disease (such as COPD or acute kidney failure). Examples of the signal metrics for assessing the pulmonary event risk may include heart rate, respiration rate or tidal volume, heart sound component such as one of the S1, S2, or S3 heart sounds, thoracic impedance, or physical activity level, among others. Examples of the signal metrics for assessing the renal event risk may include creatinine level, body urea nitrogen (BUN) level, BUN/creatinine ratio, glomerular filtration rate (GFR), or estimated glomerular filtration rate (eGFR), among others. In some examples, the risk stratifier circuit 232 may use a multivariate model such as a weighted combination of various signal metric trends to assess the cardiac event risk, pulmonary event risk, or renal event risk. FIG. 4 illustrates an example of pulmonary risk assessment, as will be discussed below.

The risk indications may have categorical values such as "high", "medium", or "low" risks that indicate the degree of the risk. The risk indications may alternatively be represented by numerical risk scores within a specified range, such as discrete values (e.g., from 0 through 5) or continuous real numbers (e.g., between 0 and 1). A larger risk score indicates a higher risk. In some examples, the risk stratifier circuit 232 may determine the risk indicators based on information about a classification of a disease, such as a classification of a WHF event into one of New York Heart Failure (NYHA) classes of one through four, a classification of a pulmonary disease such as the COPD event into one of COPD stages of one through four, or a classification of a chronic kidney disease (CKD) event into one of CKD stages of one through five. The class or stage numbers may be used to determine the numerical risk score for the corresponding first, second, or third disease.

In some examples, the risk stratifier circuit 232 may determine one or more of the risk indications at least based on clinical indications or medical history of the patient, such as exacerbation of recent chronic disease, a previous medical procedure, a clinical lab test result, patient medication intake or other treatment undertaken, or other clinical information relevant to the patient risk of developing a future disease. The information about the patient medical history may be provided by a clinician such as via the user interface 250, or stored in a memory such as an electronic medical record (EMR) system. The risk stratifier circuit 232 may receive from the clinician input or retrieve from the memory the patient medical history and adjust the disease risks accordingly. For examples, a recent HF event may put the patient at a higher risk for another cardiac event, a recent exacerbation of CKD may increase the patient risk for a WHF event, or a recent surgery may increase the risk of HF worsening such as due to intravenous fluid administration.

The patient medical history may have time-varying effect on the patient risk of developing a future disease. For example, a more recent disease state or a surgery may put the patient at higher risk for developing a cardiac, pulmonary, or renal disease than a more remote historical disease in patient medical history. To account for such time-varying effects, the risk stratifier circuit 232 may adjust one or more of the risk indications temporarily. In an example, the risk stratifier circuit 232 may produce an elevated risk above a baseline risk score within a specified timeframe following a historical medical event, and resume to the baseline risk score beyond the specified timeframe. The risk stratifier circuit 232 may alternatively or additionally produce a time-varying risk score decaying with time elapsed from a historical medical event. For example, one of the first, second, or third risk score may include at least a time-varying component determined as a linear, exponential, or other nonlinear decay function of the time elapsed from a historical medical event.

The health status analyzer circuit 230 may detect multiple diseases, such as detecting the first disease using the first detector circuit 234, detecting the second disease using the second detector circuit 236 to, and optionally detecting a third disease different than the first and second diseases using a third detector (not shown). The detectors 234 or 236 may detect the respective disease from the one or more physiological signals. In an example, the first detector circuit 234 may use one or more signal metrics such as produced by the signal processor circuit 220 to generate a first detection indication ($D_1$) of the first disease. Likewise, the second detector circuit 236 may use one or more signal metrics to generate a second detection indication ($D_2$) of the second disease, and the optional third detector circuit may use one or more signal metrics to generate a third detection indication ($D_3$). The signal metrics used by the detector circuits (e.g., 234 or 236) for detecting the respective disease may be different from the signal metrics used by the risk stratifier circuit 232 for generating the respective risk indications. In some examples, at least one signal metric for disease detection and at least one signal metric for risk indication may be generated from the same physiological signal.

The detection of the first, second, or optional third disease may be based on temporal change of signal metrics, such as a relative difference of the signal metric from a reference level representing a signal metric baseline. A disease (such as a WHF, or a COPD) may be deemed detected if the relative difference exceeds a specified threshold or falls within a specified range. In an example, the first detector circuit 234 may calculate a relative difference ($\Delta X_C$) between a representative value of a cardiac signal metric $X_C$ (e.g., a central tendency of multiple measurements of $X_C$) within a short-term time window and baseline value $X_{C-Ref}$ (e.g., a central tendency of multiple measurements of $X_C$) within a long-term time window preceding the short-term time window in time. The first detector circuit 234 may include a comparator circuit to compare the relative difference $\Delta X_C$ to a threshold, and detect the cardiac disease including generating a cardiac detection indication $D_1$ if $\Delta X_C$ falls within a specified detection range. Likewise, in an example, the second detector circuit 234 may calculate a relative difference ($\Delta X_P$) between a representative value of a pulmonary signal metric $X_P$ within a short-term time window and baseline value $X_{P-Ref}$ within a long-term time window, and detect the pulmonary disease including generating a pulmonary detection indication $D_2$ if $\Delta X_P$ falls within a specified detection range. In an example, the optional third detector circuit may calculate a relative difference ($\Delta X_R$) between a representative value of a renal signal metric $X_R$ within a short-term time window and baseline value $X_{R-Ref}$ within a long-term time window, and detect the renal disease including generating a renal detection indication $D_3$ if $\Delta X_R$ falls within a specified detection range.

The detection indications (e.g., $D_1$, $D_2$, and $D_3$) may have discrete numerical values, such as 0 indicating "no detection" and 1 indicating "detection" of the respective diseases. In some examples, one or more of the detector circuits may produce a confidence of detection (e.g., between 0 and 1), such as based on amount of deviation of the signal metric difference (e.g., $\Delta X_C$, $\Delta X_P$, or $\Delta X_R$) from the respective detection threshold. The detection indications (e.g., $D_1$, $D_2$, and $D_3$) may take continuous real numbers indicative of confidence of detection.

One or more detector circuits may be configured to detect respective diseases when one or more of the risk indications satisfy specified criteria. In an example, the first detector circuit 234 may be configured to detect a cardiac disease such as WHF in response to the first risk indication ($R_1$) exceeding a first risk threshold. Similarly, the second detector circuit 236 may be configured to detect a pulmonary disease such as COPD in response to the second risk indication ($R_2$) exceeding a second risk threshold, or the optional third detector circuit may be configured to detect a renal disease such as acute kidney failure in response to the third risk indication ($R_3$) exceeding a third risk threshold. In some examples, one or more detector circuits may be configured to detect, or withhold from detecting, a respective disease based on a comparison between the risk indications. For example, if the first risk indication $R_1$ is substantially higher than the second risk indication $R_2$ (such as by a specified margin), then the control circuit 240 may configure the first detector circuit 234 to detect a cardiac disease and configure the second detector circuit 236 to withhold from detecting a pulmonary disease. Similarly, if the second risk indication $R_2$ is substantially higher than the first risk indication $R_1$ (such as by a specified margin), then the control circuit 240 may configure the second detector circuit 236 to detect the pulmonary disease and configure the first detector circuit 234 to withhold from detecting the cardiac disease.

One or more detector circuits may be configured to detect respective diseases according to an operating mode that is determined based on the risk indications. The operating mode may include a signal metric or a detection algorithm employed by the detector circuit for detecting respective disease. In some examples, the operating mode of a detector circuit for detecting a particular disease is determined based on the risk indication of the same disease. For example, if a high cardiac risk is indicated (e.g., the first indication $R_1$ exceeds a cardiac risk threshold), then the control circuit 240 may configure the first detector circuit 234 to detect the cardiac disease using a detection algorithm with a high sensitivity or a low specificity to the cardiac disease, such as an algorithm with a lower detection threshold to which the relative difference $\Delta X_C$ is compared. Conversely, if a low cardiac risk is indicated (e.g., $R_1$ does not exceed the cardiac risk threshold), then the control circuit 240 may configure the first detector circuit 234 to detect the cardiac disease using a detection algorithm with a low sensitivity or a high specificity to the cardiac disease, such as an algorithm with a higher detection threshold for the relative difference $\Delta X_C$. The choice of detection algorithm for detecting a pulmonary or a renal disease, such as employed by the second detector circuit 236, may be similarly determined based on whether a high or low pulmonary or renal risk is indicated.

In some examples, a joint risk pattern, such as a combination of or a comparison between the first and second risk indications ($R_1$ and $R_2$), may be used to jointly determine operating modes of two or more detector circuits. By way of non-limiting examples, Table 1 shows a correspondence between the joint risk pattern ( $\{R_{HF}, R_{COPD}, R_{CKD}\}$) including risks of HF, COPD, and chronic kidney disease (CKD) and the corresponding detection algorithms employed by various cardiac disease detectors for detecting WHF, the pulmonary disease detector for detecting COPD, and the renal disease detector for detecting acute kidney disease (AKD). The correspondence may be constructed in a lookup table or association map that is stored in a memory circuit. The present inventors have recognized that an operating mode (such as detection algorithm) based at least on the joint risk pattern ($\{R_{HF}, R_{COPD}, R_{CKD}\}$) has an advantage of leveraging interactions between different disease states, such as the concomitance and interactions between WHF and various HF comorbidities. For example, according to Table 1, for a low HF risk, the WHF detection algorithm may be different depending on COPD risk and the CKD risk. Specifically, for a joint risk pattern $\{R_{HF}, R_{COPD}, R_{CKD}\}$= (Low, Low, High), the control circuit 240 may configure the first detector circuit 234 to detect the WHF using a detection algorithm with a low sensitivity or high specificity. However, for a joint risk pattern $\{R_{HF}, R_{COPD}, R_{CKD}\}$=(Low, High, High), the control circuit 240 may configure the first detector circuit 234 to detect the WHF using a detection algorithm with a moderate sensitivity or specificity.

TABLE 1

Detection algorithms based on joint risk indications.

| WHF Risk ($R_{HF}$) | COPD Risk ($R_{COPD}$) | CKD Risk ($R_{CKD}$) | WHF Detection Algorithm | COPD Detection Algorithm | AKD Detection Algorithm |
|---|---|---|---|---|---|
| Low | Low | Low | OFF | OFF | OFF |
| Low | Low | High | Low Sens/High Spec | Low Sens/ High Spec | High Sens/Low Spec |
| Low | High | High | Moderate Sens/Spec | High Sens/ Low Spec | High Sens/Low Spec |
| High | High | High | High Sens/Low Spec | High Sens/ Low Spec | High Sens/Low Spec |

A composite risk score (cR) may be computed using a combination of two or more risk scores such as $R_1$, $R_2$, and $R_3$. In an example, the composite risk score may be computed as a linear combination of $R_1$, $R_2$, and $R_3$ each weighted by the respective class numbers or stage numbers, such as NYHA classes 1-4, COPD stages of 1-4, or CKD stages of 1-5. The composite risk score cR may be used to jointly determine operating modes of two or more detector circuits. In an example, a detection algorithm with high sensitivity or low specificity may be used to detect a cardiac, pulmonary, or renal disease if a high cR is indicated (such as when cR exceeds a threshold); or a detection algorithm with low sensitivity or high specificity may be used to detect a cardiac, pulmonary, or renal disease if a low cR is indicated (such as when cR does not exceed the threshold).

The blending circuit 238 may produce a composite health status indicator (S) using the detections of the first and second diseases and the first and second risk indications ($R_1$ and $R_2$). When the optional third detector is used to generate the third detection indication $D_3$ for a third disease and the risk stratifier circuit 232 is configured to produce the third risk indication $R_3$ of the patient developing a third disease, the composite health status indicator may be computed further using $D_3$ and $R_3$. In an example, the blending circuit 238 may compute the composite health status indicator using a linear weighted combination of the first detection indication ($D_1$) of a cardiac disease such as WHF, the second detection indication ($D_2$) of a pulmonary disease such as COPD, and the third detection indication ($D_3$) of a renal disease such as AKD, that is:

$$S + w_1 \cdot D_1 + w_2 \cdot D_2 + w_3 \cdot D_3 \qquad (1)$$

The weight factors $w_1$ through $w_3$ may each be determined using the risk indications. In an example, the weight factors are chosen to be the risk scores, that is: $w_1 = R_1$, $w_2 = R_2$, and $w_3 = R_3$.

The composite health status indicator may be presented to a system user such as via a user interface 250. Additionally or alternatively, the composite health status indicator may be presented to the process such as an alert circuit for producing an alert of a deterioration of the patient's health status in response to the composite health status indicator satisfying a specified condition. Examples of alert generator based on the composite health status indicator are discussed below, such as with reference to FIG. 3.

The controller circuit 240 may control the operations of the physiological sensor circuit 210, the signal processor circuit 220, the health status analyzer circuit 230, the user interface 250, and the data and instruction flow between these components. In some examples, as previously discussed, the controller circuit 240 may configure the operations of one or more detector circuits, such as initiating or withholding the detection of a disease according to one or more risk indications, or determining the operating mode such as a detection algorithm according to one or more risk indications.

The user interface 250 may include an output unit to generate a human-perceptible presentation of the composite health status displayed on the display. In an example, at least a portion of the user interface 250 may be implemented in the external system 120. The output unit may also display information including the physiological signals and the signals metrics generated from the physiological signals, the composite health status indicator, risk indications, detection indications produced by individual detector circuits, device status such as lead impedance and integrity, battery status such as remaining lifetime of the battery, or cardiac capture threshold, among others. The information may be presented in a table, a chart, a diagram, or any other types of textual, tabular, or graphical presentation formats, for displaying to a system user. The presentation of the output information may include audio or other human-perceptible media format. The user interface 250 may also include a user input module 251, which may include an input device such as a keyboard, on-screen keyboard, mouse, trackball, touchpad, touch-screen, or other pointing or navigating devices. The input device may enable a system user such as a clinician to program the parameters used for sensing the physiological signals, assessing risk indications, and detecting various diseases.

In some examples, the patient monitoring system 200 may additionally include a therapy circuit 260 that is configured to deliver a therapy to the patient in response to one or more of the composite health status indicator, the risk indications, or the detection indications produced by individual detector circuits. Examples of the therapy may include electrostimulation therapy delivered to the heart, a nerve tissue, other target tissues in response to the detection of the target physiological event, or drug therapy including delivering drug to a tissue or organ. In some examples, composite health status indicator, the risk indications, or the detection indications may be used to modify an existing therapy, such as adjusting a stimulation parameter or drug dosage.

Figure 3:
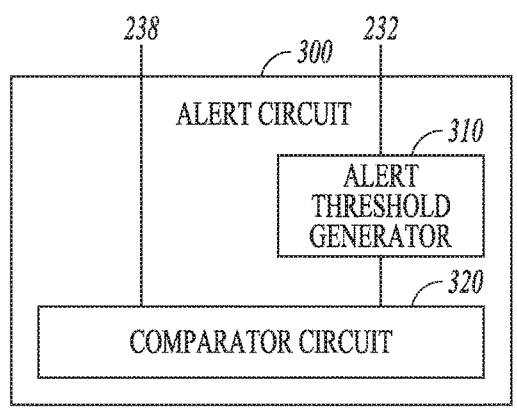
FIG. 3 illustrates generally an example of a circuit for generating an alert of deteriorating patient health status.

FIG. 3 illustrates generally an example of an alert circuit 300 for generating an alert of a deterioration of a patient health status. The alert circuit 300 may be coupled to the health status analyzer circuit 230, and generate the alert using the composite health status indicator such as generated by the blending circuit 238, and the risk indications such as generated by the risk stratifier circuit 232. The alert circuit 300 may be included within the patient monitoring system 200 and substantially included within the ambulatory system 105. Alternatively, the alert circuit 300 may be substantially included in the external system 125, or be distributed between the ambulatory system 105 and the external system 125.

The alert circuit 300 may include an alert threshold generator 310 and a comparator circuit 320. The alert threshold generator 310 may adjust a nominal or a default alert threshold stored in the memory based on the one or more risk indications produced by the risk stratifier circuit 232. In an example, the alert threshold generator 310 may increase the alert threshold if the first or second risk indication indicates a low risk of developing the first or second disease, or decrease the alert threshold if the first or second risk indication indicates a high risk of developing the first or second disease. In an example, the amount of increase or decrease of the threshold may be proportional to the numerical risk score, or be a growth function of the numerical risk score. In an example, the amount of threshold adjustment may be different across the risks of various diseases. For example, a greater amount of adjustment may be made for a high cardiac risk than for a high renal risk. The amount of threshold adjustment may be programmable by a user such as via the user interface 250. In some examples, the comparator circuit 320 may compare the composite health status indicator to the alert threshold and generate an alert of worsening health status if the composite detection score exceeds an alert threshold.

FIG. 4 illustrates generally an example of a pulmonary risk stratifier circuit 400 for assessing the patient risk of developing a future pulmonary event such as a COPD, asthma, or pulmonary edema, among others. The pulmonary risk stratifier circuit 400 may be an embodiment of at least a portion of the risk stratifier circuit 232.

The pulmonary risk stratifier circuit 400 may include one or more of a primary risk generator 410, a sampling circuit 420, a secondary risk generator 430, and a blending circuit 440. The primary risk generator 410 may be coupled to the signal processor circuit 220 to receive a plurality of measurements of at least a first pulmonary signal metric 222. The primary risk generator 410 may generate a primary pulmonary risk indication ($R_{P1}$) using a statistical measure, such a central tendency or a variability measure, of the plurality of the measurements of the first pulmonary signal metric 222. In an example, the first pulmonary signal metric 222 may be extracted from a respiration signal such as sensed using electrodes on one or more implantable leads for measuring thoracic impedance. Examples of the first pulmonary signal metric may include a respiratory rate, a tidal volume, or a rapid-shallow breathing index (RSBI) computed as a ratio of the respiration rate to the tidal volume. A patient who breathes rapidly (high respiratory rate) and shallowly (low tidal volume) tends to have a high RSBI.

In an example, the first pulmonary signal metric 222 may be extracted from a physiological signal clinically relevant to pulmonary events, such as a heart sound signal, a heart rate signal, an impedance signal, or a physical activity signal, among others. Examples of the second and third signal metrics 224 and 226 each may include intensity of a heart sound component such as a first (S1), second (S2), or third (S3) hear sound, timing of a heart sound component, systolic timing interval such as a Q wave of an ECG to S2 heart sound indicative of a pre-ejection period or a S1-to-S2 interval indicative of left-ventricular ejection time, a ratio of one heart sound component intensity to a reference intensity such as S3-to-S1 intensity ratio or S3-to-S2 intensity ratio, a heart rate measurement, a transthoracic impedance measurement, a physical activity intensity, or a time duration for the physical activity intensity falls within a specified range, among others.

The secondary risk generator 430 may generate a secondary pulmonary risk ($R_{P2}$) using at least a second pulmonary signal metric 224 and a third pulmonary signal metric 226. The second and third pulmonary signal metrics 224 and 226 may be different from the first pulmonary signal metric 222, and each extracted from a respiration signal, or a physiological signal clinically relevant to pulmonary events, as previously discussed with reference to the first pulmonary signal metric 222. In an example, the secondary risk generator 430 may generate a secondary pulmonary risk ($R_{P2}$) using a weighted combination of the second pulmonary signal metric 224 and a third pulmonary signal metric 226. In an example, the secondary risk generator 430 may generate a secondary pulmonary risk indication ($R_{P2}$) including the second pulmonary signal metric weighted by the third pulmonary signal metric.

The secondary risk generator 430 may generate the secondary pulmonary risk ($R_{P2}$) using a set of measurements of the second pulmonary signal metric 224 selected by the sampling circuit 420. The sampling circuit 420, coupled to the signal processor circuit 220, may receive the second and third pulmonary signal metrics 224 and 226, and sample a set of measurements of the second pulmonary signal metric 224 when the third signal metric 226 satisfies a specified condition. In an example, the second pulmonary signal metric 224 may include a respiratory rate and the third pulmonary signal metric 226 may include physical activity intensity or the duration of the physical activity above a threshold. The sampling circuit 420 may sample the respiratory rate measurements during a time period when a high physical activity is indicated, such as when the physical activity intensity exceeds a specified threshold. The secondary risk generator 430 may generate the secondary pulmonary risk indication ($R_{P2}$) using a statistical measure, such as a central tendency or a variability, of the sampled respiratory rate measurements produced by the sampling circuit 420.

The blending circuit 440 may combine the primary and secondary risk indications $R_{P1}$ and $R_{P2}$ to generate a composite pulmonary risk indication. The combination may include a linear weighted combination, or alternatively a nonlinear combination such as a decision tree, a neural network, a fuzzy-logic model, or a multivariate regression model, among others. In an example, the primary risk generator 410 generates the primary pulmonary risk indication $R_{P1}$ including a central tendency of the first plurality of measurements of the first signal metric, and the secondary risk generator 420 generates the secondary pulmonary risk indication $R_{P2}$ including a variability or other second-order statistics of the second plurality of measurements of the second signal metric. The blending circuit 440 may generate the composite pulmonary risk indication using a combination of the central tendency of the first signal metric and the variability of the second signal metric.

In some examples, the pulmonary risk stratifier circuit 400 may additionally receive the patient's clinical information such as medical history of the patient. The blending circuit 440 may generate the composite pulmonary risk indication further using the patient's clinical information about the patient. Examples of the clinical information may include one or more of the historical cardiac events, one or more comorbidities or other concomitant diseases states, patient physical assessment, or patient demographics such as age, gender, race, or ethnicity. In an example, the composite pulmonary risk indication may be adjusted by the clinician such as via the user interface 250 according to the patient's clinical information.

Figure 5:
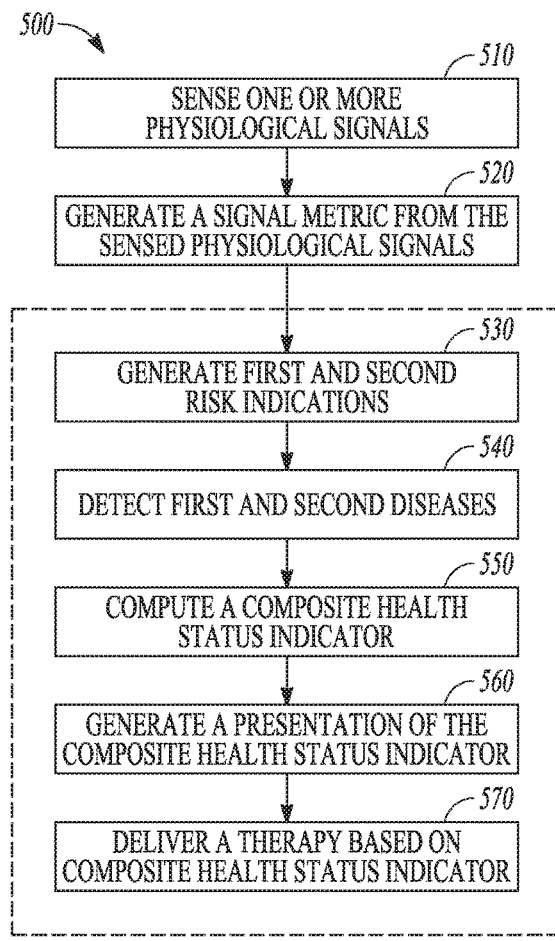
FIG. 5 illustrates generally an example of a method for assessing a patient's health status.

FIG. 5 illustrates generally an example of a method 500 for assessing a patient's health status, such as by detecting progression of multiple diseases, including cardiac, pulmonary, or renal diseases. The method 500 may be implemented and operate in an ambulatory medical device such as an implantable or wearable medical device, or in a remote patient management system. In an example, the method 500 may be executed by the health status monitor 160 or any embodiment thereof, or by the external system 125.

The method 500 begins at 510 by sensing one or more physiological signals from a patient. Examples of the physiological signals may include electrocardiograph (ECG), an electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, central venous pH value, a heart sound (HS) signal, a posture signal, a physical activity signal, or a respiration signal, among others. The physiological signals may alternatively retrieved from a storage device that stores the physiological information, such as an external programmer, an electronic medical record (EMR) system, or a memory unit, among other data storage devices.

At 520, a signal metric may be generated from the one or more physiological signals. The signal metric may include statistical or morphological parameters extracted from the sensed physiological signal. Examples of the signal metrics may include thoracic impedance magnitude, HS metrics such as intensities of heart sound components or a relative intensity such as a ratio between two heart sound components, a ratio of third (S3) heart sound intensity to a reference heart sound intensity, timing of the heart sound components with respect to a fiducial point such as a P wave, Q wave, or R wave in an ECG, a respiratory rate, a tidal volume, a RSBI, physical activity intensity, or a time duration when the activity intensity is within a specified range or above a specified threshold, systolic blood pressure, diastolic blood pressure, mean arterial pressure, or the timing metrics of these pressure measurements with respect to a fiducial point, among others. A signal metric trend may include multiple measurements of the signal metric during a specified period of time. In an example, the signal metric trend may include a daily trend including daily measurement of a signal metric over a specified number of days.

At 530, a plurality of risk indications may be produced. The risk indications may indicate the patient risks for developing multiple diseases or worsening of different disease states in the future. The risk indications may include at least a first risk indication ($R_1$) indicating the risk of the first disease and a second risk indication ($R_2$) indicating the risk of the different second disease. In an example, a third risk indication ($R_3$) indicating the risk of the third disease different from the first and second diseases may also be included. The risk indications $R_1$, $R_2$, and $R_3$ may include risks of developing a future cardiac event such as a WHF event, a future pulmonary disease such as COPD, asthma, pulmonary edema, or pulmonary hypertension, or a future renal disease such as chronic or acute kidney failure. The risk indications may have categorical values or numerical risk scores within a specified range.

The risk indications may be provided by a system user, retrieved from a memory device, or generated automatically using signal metrics derived from the one or more physiological signals. The signal metrics for assessing a cardiac risk may include heart sound components such as a S3 heart sound intensity, respiration parameters such as a respiratory rate or tidal volume measurement or a ratio of respiratory rate to tidal volume (which is also known as the rapid-shallow breathing index, RSBI), a thoracic impedance magnitude, or a physical activity intensity level measured from an physical activity signal such as using an ambulatory accelerometer associated with the patient. The signal metrics for assessing a pulmonary risk may include heart rate, respiratory rate or tidal volume, heart sound component such as one of the first, second, or third heart sounds (S1, S2, or S3, respectively), thoracic impedance, or physical activity level, among others. The signal metrics for assessing a renal risk may include creatinine level, body urea nitrogen (BUN) level, BUN/creatinine ratio, glomerular filtration rate (GFR), or estimated glomerular filtration rate (eGFR), among others. The signal metrics used for assessing the risk of one disease may also be used for assessing the risk of another different disease. In some examples, a multivariate model, such as a weighted combination of various signal metric trends, may be used to assess the cardiac event risk, pulmonary event risk, or renal event risk.

In some examples, the risk indications may be determined further using information about a classification of a disease. Examples of the disease classification may include a classification of a WHF event into one of New York Heart Failure (NYHA) classes of one through four, a classification of a pulmonary disease such as the COPD event into one of COPD stages of one through four, or a classification of a CKD event into one of CKD stages of one through five. The class numbers or stage numbers may be used to determine the numerical risk score for the corresponding first, second, or third disease, In some examples, one or more risk indications may be assessed further using clinical indications or patient medical history, such as exacerbation of recent chronic disease, a previous medical procedure, a clinical lab test result, patient medication intake or other treatment undertaken, or other clinical information relevant to the patient risk of developing a future disease. For example, a recent HF event may put the patient at a higher risk for another cardiac event, a recent exacerbation of CKD may increase the patient risk for a WHF event, or a recent surgery may increase the risk of HF worsening such as due to intravenous fluid administration. The patient medical history may have time-varying effect on the patient risk of developing a future disease. For example, a more recent disease state or a surgery may put the patient at higher risk for developing a cardiac, pulmonary, or renal disease than a more remote historical disease in patient medical history. One or more risk indications may be adjusted according to the type of clinical indications, or the time elapsed from a previous medical event. In an example, the adjustment of the risk indication based on clinical indications or medical history may be temporarily, such as to elevate the risk above a baseline risk score within a specified timeframe following a historical medical event, and resume to the baseline risk indication beyond the specified timeframe. In another example, the risk stratifier circuit 232 may produce a time-varying risk score decaying with time elapsed from a historical medical event.

In an example, a method of pulmonary risk stratification may be used to generate from one or more signal metrics a pulmonary risk indication indicating patient risk of developing a future pulmonary event such as a COPD, asthma, or pulmonary edema, among others. The method may be implemented an executed in pulmonary risk stratifier circuit 400 as illustrated in FIG. 4. A primary pulmonary risk indication may be determined as a statistical measure, such a central tendency or a variability measure, of the plurality of the measurements of a first pulmonary signal metric. Examples of the first pulmonary risk may include a respiratory rate, a tidal volume, or a rapid-shallow breathing index (RSBI) computed as a ratio of the respiration rate to the tidal volume. A secondary pulmonary risk ($R_{P2}$) may be determined using at least a second pulmonary signal metric and a third pulmonary signal metric. The second and third pulmonary signal metrics may be different from the first pulmonary signal metric, and each extracted from a respiration signal, or a physiological signal clinically relevant to pulmonary events, as previously discussed with reference to the first pulmonary signal metric. In an example, the secondary pulmonary risk ($R_{P2}$) may be determined as a weighted combination of the second pulmonary signal metric and a third pulmonary signal metric. In another example, $R_{P2}$ may include the second pulmonary signal metric weighted by the third pulmonary signal metric. In an example, the second pulmonary signal metric may be sampled when the third signal metric satisfies a specified condition (such as exceeding a threshold). $R_{P2}$ may be generated as a statistical measure, such as a central tendency or variability, of the sampled measurements of the second pulmonary signal metric. The primary and secondary risk indications $R_{P1}$ and $R_{P2}$ may then be combined to generate a composite pulmonary risk indication.

At 540, multiple diseases may be detected from the one or more physiological signals, which may include cardiac diseases such as WHF, pulmonary diseases such as COPD, or renal diseases such as acute kidney failure. The signal metrics for detecting the respective disease may be different from the signal metrics for generating the respective risk indications. In an example, the detection of multiple diseases may be based on temporal change of signal metrics, such as a relative difference of the signal metric from a reference level representing a signal metric baseline. Numerical detection indications (e.g., $D_1$, $D_2$, and $D_3$) may be generated to indicate "no detection" (e.g., $D_1$=0) or "detection" (e.g., $D_1$=1) of the respective diseases. In some examples, one or more detection indications may take continuous real numbers (e.g., between 0 and 1) indicative of confidence of detection.

The detection of first or second disease may be conditional upon the one or more risk indications satisfying specified criteria. In an example, detection of a cardiac disease such as WHF is activated in response to the cardiac risk indication exceeding a first risk threshold. Similarly, detection of a pulmonary disease such as COPD may be activated in response to the pulmonary risk indication exceeding a second risk threshold, and detection of a renal disease such as acute kidney failure may be activated in response to the renal risk indication exceeding a third risk threshold. In some examples, activating the detection of one disease or withholding the detection of another disease may be based a comparison between different risk indications. For example, if the cardiac risk indication is substantially higher than the pulmonary risk indication (such as by a specified margin), then the detection of cardiac disease is turned on, while the detection of pulmonary disease may be withheld at least temporarily.

The first or second disease may be detected according to a specified operating mode. The operating mode may include a signal metric or a detection algorithm of detecting respective disease. The operating mode used for detecting a particular disease may be determined based on the risk indication of the same disease. In an example, if a cardiac risk indication exceeds a risk threshold and thus indicates a relatively high cardiac risk, then the cardiac disease (e.g., WHF) may be detected according to a first operating mode, which may include a first detection algorithm. However, if the cardiac risk indication falls below the risk threshold and thus indicates a relatively low cardiac risk, then the cardiac disease may be detected according to a second operating mode, which may include a second detection algorithm. Compared to the second algorithm, the first detection algorithm may be more sensitive, or less specific, to the first or second disease. The detection algorithms for detecting various diseases may alternatively be based on a joint risk pattern, such as a combination of or a comparison between risk indications, such as the example illustrated in Table 1.

At 550, a composite health status indicator may be computed using the detections of at least the first and second diseases and the risk indications associated with the first and second diseases. The composite health status indicator may be computed using a linear combination of cardiac, pulmonary, and renal detection indications each weighted by respective risk indications, such as discussed above with reference to Equation (1).

At 560, a human-perceptible presentation of the composite health status indicator may be generated, and displayed such as on the user interface 250. The information may be presented in a table, a chart, a diagram, or any other types of textual, tabular, or graphical presentation formats. The composite health status indicator may additionally or alternatively be presented to the process such as for producing an alert of a deterioration of the patient's health status. The alert may be generated in response to the composite health status indicator satisfying a specified condition, such as exceeding an alert threshold. In some examples, the alert threshold may be determined using one or more risk indications. Examples of generating an alert based on the composite health status indicator, and alert threshold based on risk indications, are discussed below, such as with reference to FIGS. 6-7.

The method 500 may additionally include a step 570 of delivering a therapy to the patient in response to one or more of the composite health status indicator, the risk indications, or the detection indications produced by individual detector circuits. Examples of the therapy may include electrostimulation therapy delivered to the heart, a nerve tissue, other target tissues in response to the detection of the target physiological event, or drug therapy including delivering drug to a tissue or organ. In some examples, at 570, the composite health status indicator, the risk indications, or the detection indications may be used to modify an existing therapy, such as adjusting a stimulation parameter or drug dosage.

Figure 6:
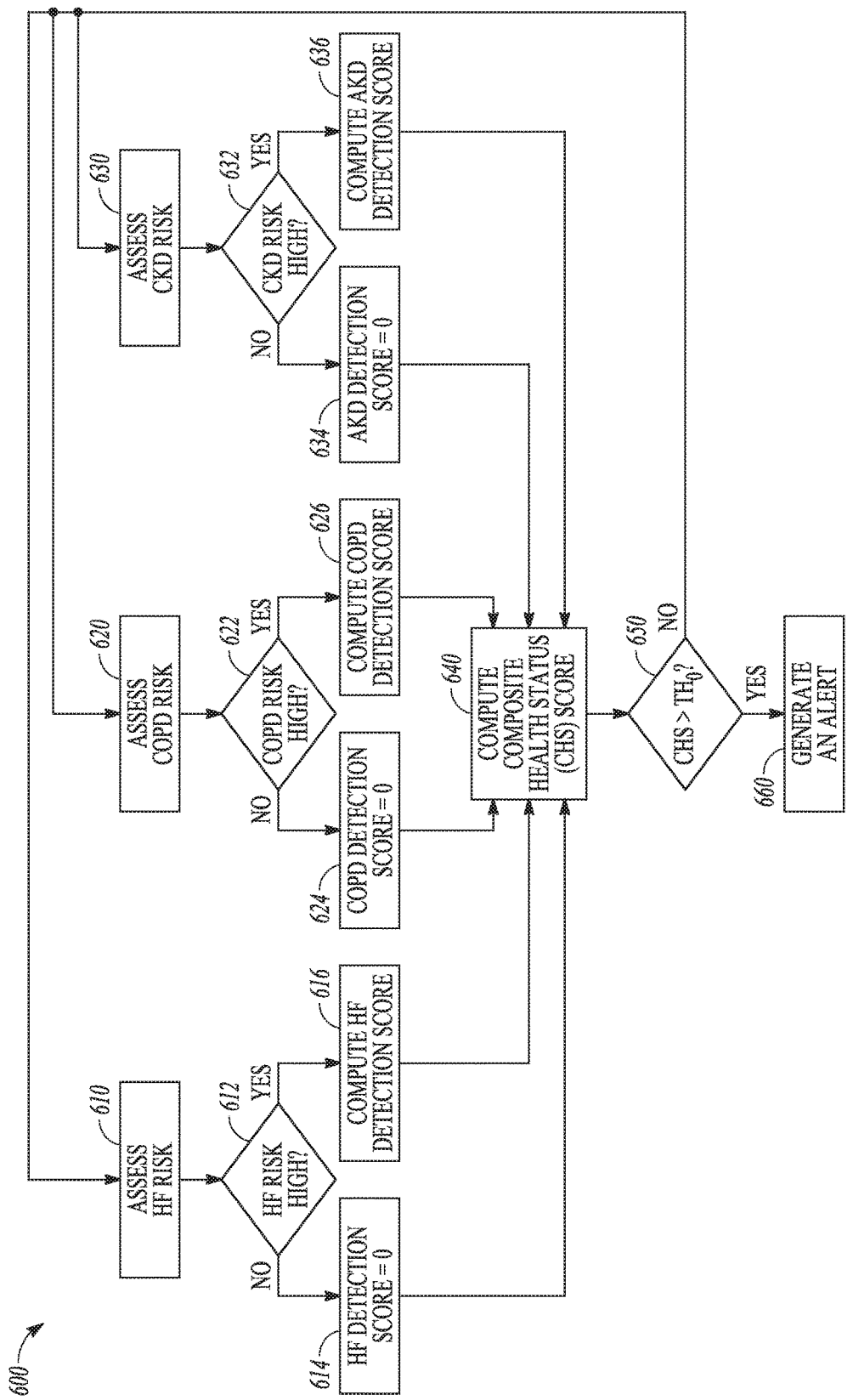
FIG. 6 illustrates generally an example of a method for computing a composite health status (CHS) indicator and generating an alert using the CHS indicator.

FIG. 6 illustrates generally an example of a method 600 for computing a composite health status (CHS) indicator and generating an alert based on the CHS indicator. The method 600 may be an embodiment of at least portions of the method 500, such as steps 530-560 of the method 500. In an example, the method 600 may be implemented in and executed by the patient monitoring system 200 as illustrated in FIG. 2.

The method 600 begins at 610, 620 and 630 by assessing cardiac, pulmonary, and renal disks. Risk indications associated with HF, COPD and chronic kidney disease (CKD) may be provided by a system user or generated using signal metrics derived from the one or more physiological signals. If at 612 the HF risk exceeds a cardiac risk threshold such that a high risk is indicated, then a HF detection score ($D_{HF}$) may be generated at 616. The detection score $D_{HF}$ may take discrete values indicating a detection ($D_{HF}=1$) or no detection ($D_{HF}=0$) of the WHF event, or continuous real numbers indicative of confidence of detection, such as such as based on amount of deviation of the signal metric difference (e.g., $\Delta X_C$, $\Delta X_P$, $\Delta X_R$) from the respective detection threshold. If at 612 the HF risk falls below the cardiac risk threshold such that a low risk is indicated, then the HF detection process is withheld, and a HF detection score of zero ($D_{HF}=0$) is assigned at 614. Similarly, if at 622 a high COPD risk is indicated, then a COPD detection process may be activated and a COPD detection score ($D_{COPD}$) may be generated at 626. If a low COPD risk is indicated, then the COPD detection process is withheld and a COPD detection score of zero ($D_{COPD}=0$) is assigned at 624. Likewise, if at 632 a high CKD risk is indicated, then a process of acute kidney disease (AKD) detection may be activated, and an AKD detection score ($D_{AKD}$) may be generated at 636. If a low CKD risk is indicated, then the AKD detection process is withheld and an AKD detection score of zero ($D_{AKD}=0$) is assigned at 634.

At 640, a composite health status (CHS) score may be generated using a weighted combination of the detection indications $D_{HF}$, $D_{COPD}$, and $D_{AKD}$, such as according to Equation (1). In some examples, one or more of the HF detection, the COPD detection, or the AKD detection may be activated even if the corresponding risk indication is low. The risk indications may include numerical risk scores such as discrete values (e.g., from 0 through 5) or continuous real numbers (e.g., between 0 and 1), or based on disease classification such as New York Heart Failure (NYHA) classes of one through four, COPD event into one of COPD stages of one through four, or CKD stages of one through five. The CHS score at 640 may be computed as a combination of the detection indications each weighted by their respective risk scores.

At 650, the composite health status (CHS) may be compared to an alert threshold $TH_0$. If the CHS score exceeds the threshold $TH_0$, an alert may be generated at 660, indicating a deterioration of patient health status or exacerbation of multiple diseases. If the CHS score does not exceed the threshold $TH_0$, then the process may proceed to 610, 620 and 630 to continue assessing the cardiac, pulmonary and renal risks.

Figure 7:
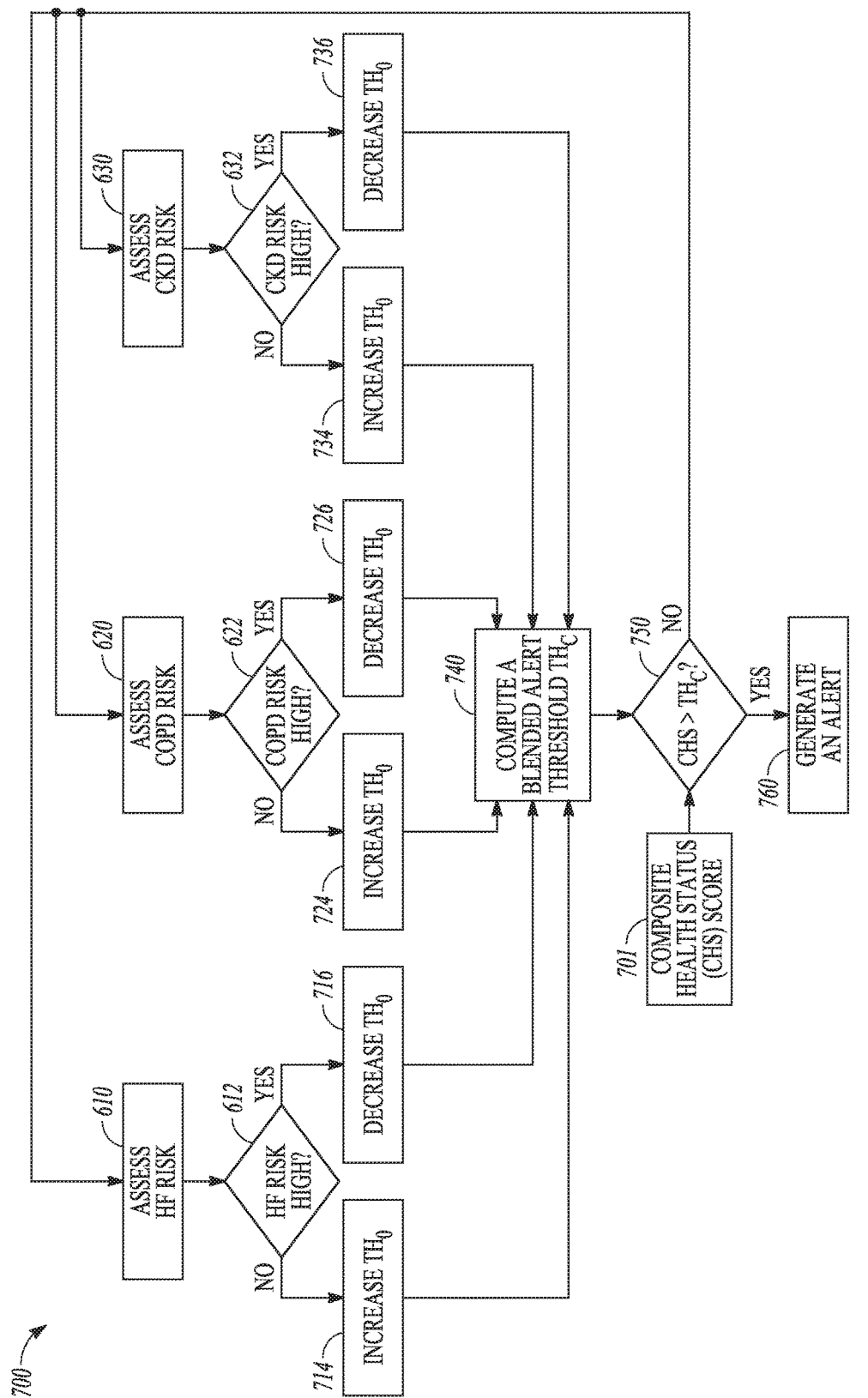
FIG. 7 illustrates generally an example of a method for computing a blended alert threshold.

FIG. 7 illustrates generally an example of a method 700 for computing a blended alert threshold $TH_C$. The method 700 may be an embodiment of at least portions of the method 500, such as steps 530-560 of the method 500. In an example, the method 700 may be implemented in and executed by the patient monitoring system 200 as illustrated in FIG. 2. Portions of the method 700 may be implemented in and executed by the alert circuit 300 as illustrated in FIG. 3.

The method 700 may include the steps of assessing cardiac, pulmonary, and renal disks and generating risk indications associated with HF, CORD and CKD at 610, 620 and 630. Based on the comparisons of the risk indications to their respective risk thresholds at 612, 622 and 632, the nominal alert threshold $TH_0$ may be adjusted. For example, if at 612 a high HF risk is indicated, then the threshold $TH_0$ may be decreased at 716. Decreasing the alert threshold may increase the likelihood that the composite health status (CHS) score, such as that obtained at 640 in FIG. 6, exceeds the alert threshold; thus an alert is more likely to be generated for patient having a higher cardiac risk than for patients having a relatively lower cardiac risk. Similar risk-based adjustment of alert threshold may be applied to pulmonary risk and renal risk. For example, the alert threshold $TH_0$ may be increased at 724 if a low COPD risk is indicated or decreased at 726 if a high COPD risk is indicated, and the alert threshold $TH_0$ may be increased at 734 if a low CKD risk is indicated or decreased at 736 if a high CKD risk is indicated. In an example, the amount of increase or decrease of the threshold may be proportional to the numerical risk score, or be a growth function of the numerical risk score, such that a higher risk corresponds to greater decrease in the threshold $TH_0$. The amount of threshold adjustment may be different across the risks of various diseases. For example, a greater amount of adjustment may be made for a high cardiac risk than for a high renal risk.

At 740, a blended alert threshold ($TH_C$) may be generated by combining the risk-based adjustments according to the HF risk, COPD risk, and the CKD risk. The composite health status (CHS) score at 701, which may be the CHS score at 640 that is generated using method 600, may be compared to the blended alert threshold $TH_C$ at 750. An alert may be generated at 760 if the CHS score exceeds the threshold $TH_C$. However, if the CHS score falls below the threshold $TH_C$, then the process may proceed to 610, 620 and 630 to continue assessing the cardiac, pulmonary and renal risks.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMS), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system for monitoring health status of a patient, the system comprising:

a physiological sensor circuit including a sense amplifier circuit configured to sense one or more physiological signals;

a health status analyzer circuit coupled to the physiological sensor circuit, the health status analyzer circuit including:
- a risk stratifier circuit configured to:
  - calculate a first risk score of the patient developing a first disease using a first risk algorithm and first physiological signal metrics; and
  - calculate a second risk score of the patient developing a different second disease using a second risk algorithm different from the first risk algorithm and second physiological signal metrics;
- a first detector circuit configured to automatically determine a status of the first disease using the one or more physiological signals and the first risk score;
- a second detector circuit configured to automatically determine a status of the second disease using the one or more physiological signals and the second risk score;
- a blending circuit configured to generate a composite health status indicator using the determined status of the first disease and the determined status of the second disease; and
- an output circuit configured to generate an alert of worsening health status if the composite health status indicator exceeds an alert threshold.

2. The system of claim 1, wherein:
the first disease is heart failure;
the second disease is a pulmonary disease or a renal disease; and
the blending circuit is configured to generate the composite health status indicator using a weighted combination of the determined status of the first disease and the determined status of the second disease.

3. The system of claim 2, wherein the risk stratifier circuit is to calculate the second risk score of the patient developing the pulmonary disease using both primary and secondary pulmonary risk scores, and
wherein the primary pulmonary risk score is based on a first pulmonary signal metric and the secondary pulmonary risk score is based on second and third pulmonary signal metrics.

4. The system of claim 3, wherein the risk stratifier circuit is configured to calculate the secondary pulmonary risk score using the second pulmonary signal metric weighted by the third pulmonary signal metric.

5. The system of claim 3, wherein the risk stratifier circuit is configured to calculate the secondary pulmonary risk score using a plurality of measurements of the second pulmonary signal metric when the third pulmonary signal metric satisfies a specified condition.

6. The system of claim 1, wherein at least one of:
the first detector circuit is configured to automatically determine the status of the first disease in response to the first risk score exceeding a first risk threshold; or
the second detector circuit is configured to automatically determine the status of the second disease in response to the second risk score exceeding a second risk threshold.

7. The system of claim 1, wherein:
in response to the first risk score being higher than the second risk score by a first margin, the first detector is configured to automatically determine the status of the first disease, and the second detector is configured to withhold determining the status of the second disease; or in response to the second risk score being higher than the first risk score by a second margin, the second detector is configured to automatically determine the status of the second disease, and the first detector is configured to withhold determining the status of the first disease.

8. The system of claim 1, wherein at least one of the first or second detector circuit is configured to:
automatically determine the status of the first or second disease according to a first operating mode if the first or second risk score exceeds a risk threshold; and
automatically determine the status of the first or second disease according to a second operating mode if the first or second risk score does not exceed the risk threshold; and
wherein the first operating mode includes a first detection algorithm different from the first risk algorithm, and the second operating mode includes a second detection algorithm different from the second risk algorithm.

9. The system of claim 8, wherein the operating mode for determining the status of the respective first or second disease is based on a joint risk pattern including the first risk score relative to the second risk score.

10. The system of claim 1, wherein:
the first detector circuit is to automatically determine the status of the first disease including generating a first detection score indicating a confidence of the automatically determined status of the first disease;
the second detector circuit is to automatically determine the status of the second disease including generating a second detection score indicating a confidence of the determined status of the second disease; and
the blending circuit is to generate the composite health status indicator including a composite detection score using a combination of the first and second detection scores each weighted by the respective first and second risk scores.

11. The system of claim 10, wherein the risk stratifier circuit is configured to calculate the first or second risk score using information about a classification of the first or second disease including:
a classification of a worsening heart failure (WHF) event into one of New York Heart Failure classes one through four;
a classification of a pulmonary disease into one of Chronic Obstructive Pulmonary Disease stages one through four; or
a classification of a chronic kidney disease (CKD) into one of CKD stages one through five.

12. The system of claim 1, wherein:
the first detector circuit is configured to automatically determine the status of the first disease using a third signal metric derived from the one or more physiological signals different from the first signal metrics for calculating the first risk score; or
the second detector circuit is configured to automatically determine the status of the second disease using a fourth signal metric derived from the one or more physiological signals different from the second signal metrics for calculating the second risk score.

13. A method for monitoring health status of a patient via a monitoring system, the method comprising:
sensing one or more physiological signals via a physiological sensor circuit;
calculating, via a risk stratifier circuit, a first risk score of the patient developing a first disease using a first risk algorithm and first physiological signal metrics;

calculating, via the risk stratifier circuit, a second risk score of the patient developing a different second disease using a second risk algorithm different from the first risk algorithm and second physiological signal metrics;

automatically determining a status of the first disease using the one or more physiological signals and the first risk score via a first detector circuit;

automatically determining a status of the second disease using the one or more physiological signals and the second risk score via a second detector circuit;

computing, via a blending circuit, a composite health status indicator using the determined status of the first disease and the determined status of the second disease; and generating an alert of worsening health status if the composite health status indicator exceeds an alert threshold.

14. The method of claim 13, wherein the first disease is heart failure and the second disease is a pulmonary disease, the method further comprising:

calculating a third risk score of the patient developing a renal disease; and automatically determining a status of the renal disease using the one or more physiological signals and the third risk score;

wherein computing the composite health status indicator includes using a weighted combination of the determined status of the heart failure, the determined status of the pulmonary disease, and the determined status of the renal disease.

15. The method of claim 13, wherein automatically determining the status of the first disease and the status of the second disease includes:

in response to the first risk score being higher than the second risk score by a first margin, automatically determining the status of the first disease and withholding determining the status of the second disease; or in response to the second risk score being higher than the first risk score by a second margin, automatically determining the status of the second disease and withholding determining the status of the first disease.

16. The method of claim 13, wherein automatically determining the status of the first disease and the status of the second disease includes:

automatically determining the status of the first or the second disease according to a first operating mode if the first or second risk score exceeds a risk threshold; and automatically determining the status of the first or the second disease according to a second operating mode if the first or second risk score does not exceed the risk threshold; and wherein the first operating mode includes a first detection algorithm and the second operating mode includes a second detection algorithm.

17. The method of claim 13, wherein automatically determining the status of the first disease and the status of the second disease includes generating a first detection score indicating a confidence of the determined status of the first disease and a second detection score indicating a confidence of the determined status of the second disease; and wherein the composite health status indicator is computed using a combination of the first and second detection scores each weighted by the respective first and second risk scores.

18. A system for monitoring health status of a patient, the system comprising:

a health status analyzer circuit configured to:

calculate a first risk score of the patient developing a first disease using a first risk algorithm and first physiological signal metrics;

calculate a second risk score of the patient developing a second disease different than the first disease using a second risk algorithm different from the first risk algorithm and second physiological signal metrics;

generate a first detection score indicating a confidence of a status of the first disease using one or more physiological signals sensed from the patient;

generate a second detection score indicating a confidence of a status of the second disease using the one or more physiological signals sensed from the patient; and generate a composite detection score using the first and second detection scores; and determine an alert threshold using at least one of the first or second risk score; and an output circuit configured to generate an alert of worsening health status if the composite detection score exceeds the determined alert threshold.

19. The system of claim 18, wherein the health status analyzer circuit is configured to:

determine a first adjustment of a nominal alert threshold based on the first risk score;

determine a second adjustment of the nominal alert threshold based on the second risk score; and determine the alert threshold using the first and second adjustments of the nominal alert threshold.

20. The system of claim 19, wherein:

the first adjustment of the nominal alert threshold includes a first decrease of the nominal alert threshold if the first risk score exceeds a first risk threshold, and a first increase of the nominal alert threshold if the first risk score falls below the first risk threshold; and the second adjustment of the nominal alert threshold includes a second decrease of the nominal alert threshold if the second risk score exceeds a second risk threshold, and a second increase of the nominal alert threshold if the second risk score falls below the second risk threshold.

* * * * *